Figure 3:
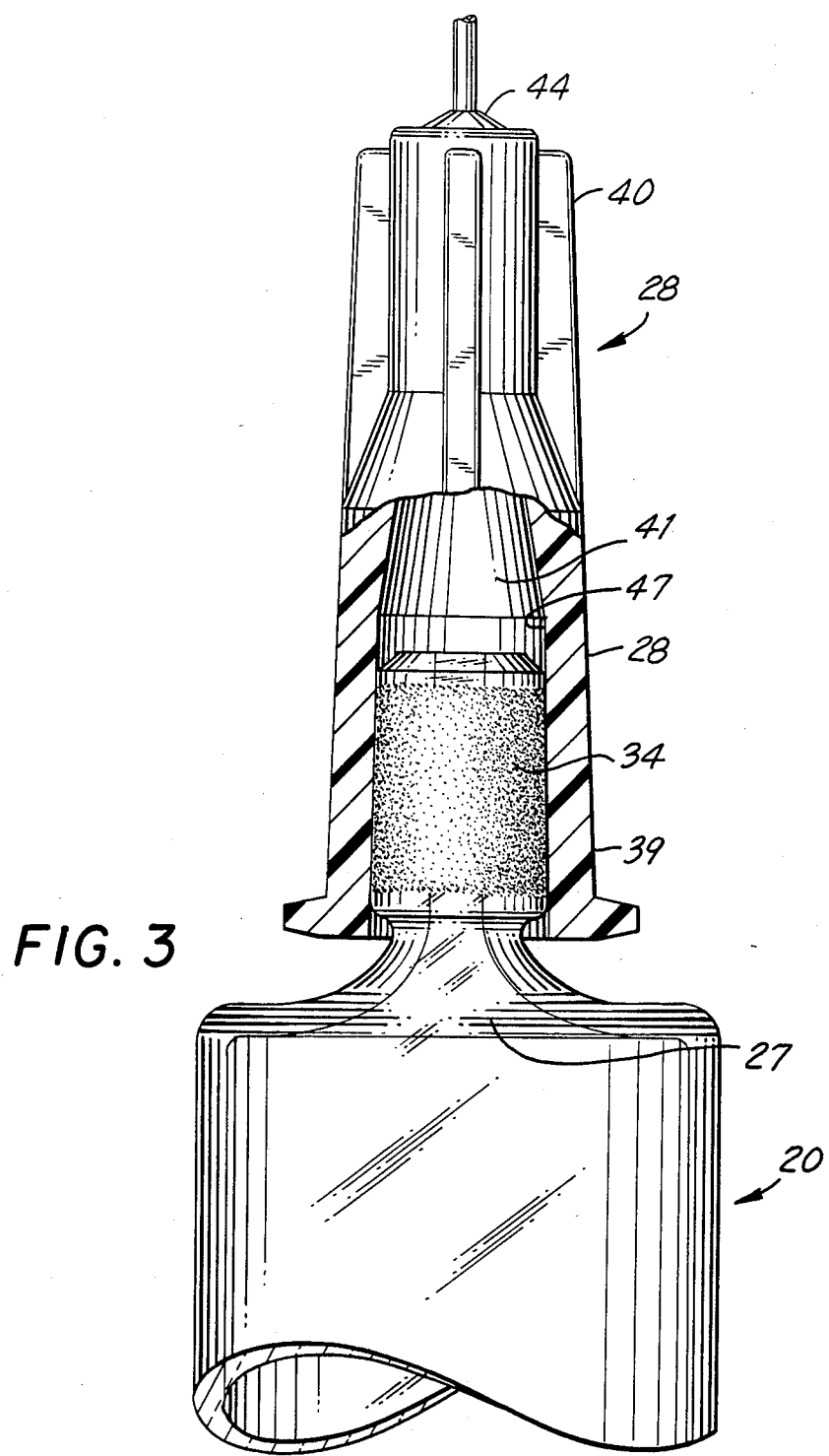

United States Patent [19]

Imbert

[11] Patent Number: 4,589,871
[45] Date of Patent: May 20, 1986

[54] SYRINGE BARREL

[75] Inventor: Claude Imbert, La Tronche, France

[73] Assignee: Becton, Dickinson and Company, Paramus, N.J.

[21] Appl. No.: 717,748

[22] Filed: Mar. 29, 1985

[51] Int. Cl.⁴ .............................................. A61M 5/325
[52] U.S. Cl. .................................. 604/240; 29/402.18
[58] Field of Search ........................ 604/240, 241, 243; 29/402.18, 419 G, 428, 458, 459, 460

[56] References Cited

U.S. PATENT DOCUMENTS 2,811,155  10/1957  Dunnican .
2,842,125   7/1958  Stephany ............................ 604/240
3,402,713   9/1968  Senkowski et al. .
4,430,080   2/1984  Pasquini et al. ..................... 604/240

FOREIGN PATENT DOCUMENTS 3520  of 1891  United Kingdom ................ 604/241
494921  11/1938  United Kingdom ................ 604/240

Primary Examiner—John D. Yasko
Attorney, Agent, or Firm—John L. Voellmicke

[57] ABSTRACT

A syringe barrel includes an elongate barrel portion having a chamber for retaining fluid and a tip extending from a distal end of the barrel portion having a passageway therethrough communicating with the chamber. A coating on the tip increases the roughness of the tip so that the force required to remove a fluid transfer apparatus, removably connected to the tip by a frictional interference fit, is greater than the force required to remove the fluid transfer apparatus from an identically sized tip without the coating.

16 Claims, 5 Drawing Figures

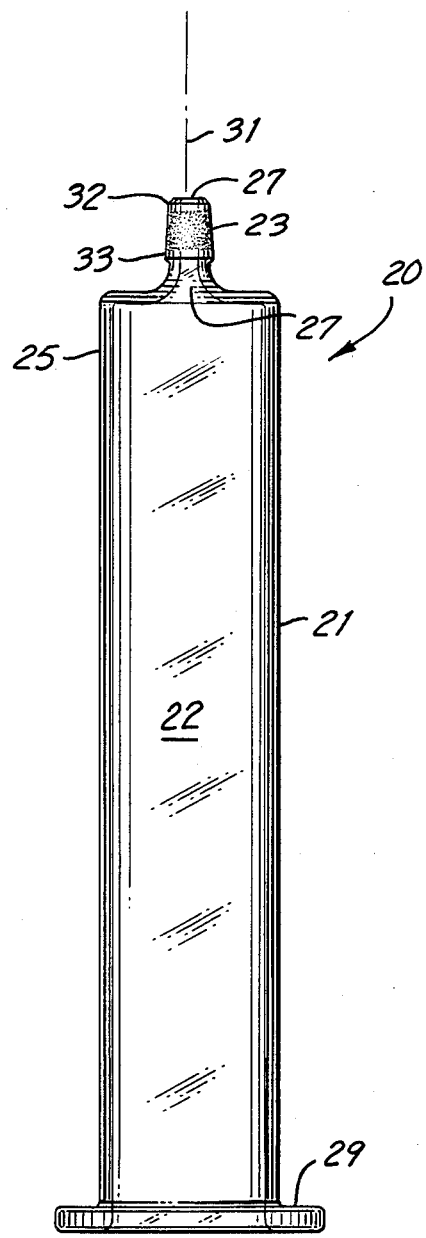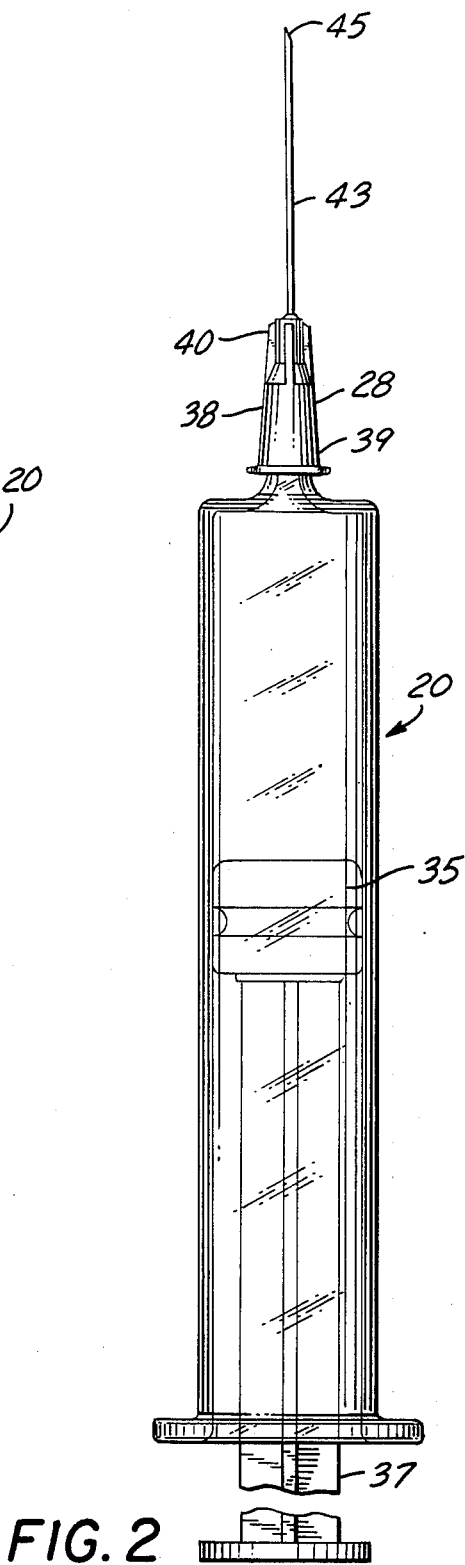

SYRINGE BARREL

BACKGROUND OF THE INVENTION

1. Field of the Invention

The present invention relates to a syringe barrel and more particularly concerns a syringe barrel having a tip which is coated to increase the roughness of the tip and a method of making same.

2. Description of the Prior Art

Generally speaking, a hypodermic syringe consists of a cylindrical barrel, most commonly made of thermoplastic material or glass, with a distal end adapted to be connected to a hypodermic needle and a proximal end adapted to receive a stopper and plunger rod assembly. One of the purposes of the stopper is to provide a relatively air tight seal between itself and the syringe barrel so that movement of the stopper up and down the barrel will cause liquid, blood or other fluids to be drawn into or forced out of the syringe through the distal end. The stopper is moved along the syringe barrel by applying axial force on a rigid plunger rod which is connected to the stopper and is sufficiently long to be accessible outside of the barrel.

Hypodermic needle assemblies, typically including a cannula and a hub, are often times removably attached to syringes for performing a variety of tasks such as the delivery of medication into patients and into devices, and for withdrawing fluid samples from patients and from fluid sources. Usually, the hub of the hypodermic needle assembly has tapered interior surface adapted to engage the tapered tip of the syringe barrel so that the two components are joined in a frictional interference fit. The tapered syringe tip and the complementarily tapered receptacle in the hub are referred to as standard luer fittings. A wide variety of other devices such as stopcocks and tubing sets have standard luer fittings which allow them to be engaged to a syringe tip.

It is important that the frictional fit between the syringe tip and the needle hub or other device is strong enough to prevent accidental disengagement caused by the fluid pressures withing the syringe and/or other factors. If the syringe tip becomes disengaged from the other fluid delivery means, medications, blood or other fluid will be lost and also there is potential for contamination of fluid.

To improve the strength of the interference fit between the syringe tip and the fluid delivery device, such as a hypodermic needle, many prior art devices provide a circular internally threaded receptacle which is concentric to and larger than the luer tip of the syringe barrel. The hypodermic needle or other fitting used with this type of syringe has wings projecting radially outwardly from the base of the needle hub so that the needle hub may be placed on the syringe tip and rotated in a clockwise direction until the hub wings engage the threads at the syringe tip and pull the needle hub into tight frictional engagement with the syringe tip. This type of fitting is commonly referred to as a luer lock. With a plastic syringe barrel the threaded luer lock collar can be molded integrally with the syringe barrel as taught in U.S. Pat. No. 3,402,713 to Senkowski et al. When using a glass syringe barrel the threaded collar is usually made of a relatively expensive metal part which is chrome plated and attached to the glass syringe. Such a device is taught in U.S. Pat. No. 2,711,171 to Dunnican. The type of device taught by Dunnican is commonly found on reusable glass syringes. However, its relative expense, makes it impractical for a disposable syringe assembly.

It is also common practice to blast the tip of a glass syringe with abrasive particles, such as aluminum oxide beads or sand, to increase the roughness of the tip and, therefore, the strength of the frictional interference fit between the syringe tip and the needle hub. The roughened surface also is believed to be helpful in the event that liquid is accidentally deposited on the syringe tip, because the roughened surface is better able to break through the liquid film as the needle hub is engaged thereon. A disadvantage of abrasive blasting a syringe tip to obtain a roughened surface is that the debris created by the blasting process must be thoroughly and completely removed from the syringe barrel. This clean up operation is an expensive secondary operation which is required because of the medical uses most syringes are placed in.

Although the prior art, as alluded to above, teaches various devices and structures for improving the frictional interference fit between a syringe barrel and a hypodermic needle assembly hub or other fluid handling device, there is still a need for a simple, straightforward, reliable hypodermic syringe barrel having a tip which facilitates the improved frictional interference fit between the barrel and the hypodermic hub or other fluid handling device. It is desirable that the syringe barrel provide the improved fit without additional structure or processing steps which are expensive to carry out and require subsequent cleaning operations thereafter.

SUMMARY OF THE INVENTION

A syringe barrel of the present invention comprises a barrel portion having a chamber for retaining fluid and a tip extending from a distal end of the barrel portion. This tip includes a passageway therethrough communicating with the chamber. Coating means on the tip is provided for increasing the roughness of the tip.

In accordance with another embodiment of the present invention, a syringe barrel comprises an elongate barrel portion having a chamber for retaining fluid and a tip extending from a distal end of the barrel having a passageway therethrough communicating with the chamber. This tip is frusto-conically shaped and has a smaller outside diameter at the distal end of the tip than at the proximal end of the tip. A coating is provided on the tip for increasing the roughness of the tip so that the force required to remove a fluid transfer apparatus, such as a hypodermic needle assembly hub, removably connected to the tip by a frictional interference fit, is greater than the force required to remove the fluid transfer apparatus from an identically sized tip without the coating.

In accordance with another aspect of the present invention, a method of increasing the roughness of the tip of a syringe barrel, so that the force required to remove a fluid transfer apparatus removably connected to the tip by a frictional interference fit is greater than the force required to remove the fluid transfer apparatus from an identically sized tip without the coating, includes selecting, in a selecting step, a syringe barrel. The syringe barrel includes an elongate barrel portion having a chamber for retaining fluid and a tip extending from a distal end of the barrel portion having a passageway therethrough communicating with the chamber. Depositing, in a coating step, a suspension including a liquid carrier and solid particles so that the suspension is deposited on the tip. Transferring the syringe barrel to a heated area having a temperature high enough to vaporize a portion of the carrier and to cause the particles to fixedly attach to the tip. Removing the syringe barrel from the heated area completes the process.

In accordance with the principles of the present invention, a number of advantages are achieved. Primarily the present invention provides a simple, straightforward, reliable, easily fabricated syringe barrel having a coating on the tip thereof for increasing the roughness of the tip. The instant invention eliminates the need for debris generating roughening procedures such as abrasive blasting or grinding to produce a syringe barrel with a roughened tip. The instant invention also eliminates the extensive clean up process which necessarily follows the aforementioned debris generating procedures. The instant invention also includes a method for producing a syringe barrel having a coating on its tip for increasing the roughness of the tip.

BRIEF DESCRIPTION OF THE DRAWINGS

FIG. 1 is a side elevation view of the preferred syringe barrel of the present invention;

FIG. 2 is a side elevation view of a syringe assembly using the syringe barrel of the present invention;

FIG. 3 is an enlarged partially cross-sectioned view of the distal end of the syringe assembly of FIG. 2, illustrating the frictional interference fit between the tip of the syringe barrel and the needle assembly hub;

FIG. 4 is an enlarged side elevation view of the distal end of the syringe barrel of the present invention; and FIG. 5 is a perspective view of an apparatus applying the coating of the present invention to a syringe barrel tip.

DETAILED DESCRIPTION

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1 through 4, a syringe barrel 20 includes an elongate barrel portion 21 having a chamber 22 for retaining fluids. A tip 23 extends from a distal end 25 of the barrel and contains a passageway 27 therethrough communicating with chamber 22. For the purposes of the description of the present invention, the term "distal end" is meant to refer to the end furthest from the person holding the syringe barrel, whereas the term "proximal end" is meant to refer to the end closest to the holder of the syringe. Tip 23 is preferably adapted to accept a hypodermic needle assembly 28, as will be described in more detail hereinafter. However, the tip may be adapted to engage other fluid transfer apparatus. A flange 29 may also be provided at the proximal end of the barrel to facilitate the handling and the positioning of the syringe.

Tip 23 runs along longitudinal axis 31 of the syringe barrel and is preferably frusto-conically shaped, having a smaller outside diameter at a distal end 32 of the tip than at a proximal end 33 of the tip. It should be noted that it is within the purview of the instant invention to include syringe barrels having tips with other shapes such as a cylindrically shaped tip having a substantially uniform outside diameter, and the like. A coating 34 on the frusto-conically shaped surface of tip increases the roughness of the tip so that the force required to remove a fluid transfer apparatus, such as hypodermic needle assembly 28, connected to the tip by a frictional interference fit is greater than the force required to remove the fluid transfer apparatus from an identically sized tip without the coating.

The syringe barrel of the instant invention may be used in a hypodermic syringe assembly which includes syringe barrel 20, hypodermic needle assembly 28, a resilient stopper 35 and a rigid plunger rod 37. The resilient stopper is slidably positioned in fluid-tight engagement inside barrel portion 21. Stopper 35 engages plunger rod 37. In this embodiment the stopper contains an internal thread (not shown) which engages an external thread (not shown) on the plunger rod. It will be apparent to one skilled in the art that numerous constructions can be used to join a stopper and a plunger rod and that the arrangement described above is exemplary of these many possibilities. The plunger rod is accessible outside of the proximal end of the syringe barrel and is provided to move the stopper along the barrel to force fluid into or out of chamber 22 through passageway 27. Specifically, the stopper is capable of moving fluid from the chamber through the passageway upon its movement toward the distal end of the barrel, and the stopper is capable of facilitating the drawing of fluid into the chamber through the tip passageway upon its movement away from the distal end of the barrel.

Hypodermic needle assembly 28 includes a hub 38, having a proximal end 39, a distal end 40, and a passageway 41 therethrough. A cannula 43 having a lumen (not shown) therethrough is connected to the distal end of the hub using epoxy 44 so that the lumen of the cannula is in fluid communication with passageway 41 of the hub. The cannula also includes sharpened distal tip 45 adapted to pierce a patient's flesh or other piercible means for the purpose of transferring fluid. Accordingly, movement of the stopper toward the distal end of syringe barrel 20 causes fluid to flow from the barrel through passageway 27 in the barrel, through passageway 41 and through the lumen of the cannula and out the distal sharpened end thereof.

Needle assemblies and syringes are constructed so that the needle assembly may be removably connected to the syringe tip. For example many syringes have a frusto-conically shaped tip which is adapted to engage a frusto-conically shaped passageway, such as frusto-conically shaped portion 47 of hub 28. Forcing the hub toward the syringe tip will cause the frusto-conically shaped tip to engage the corresponding hub portion in a frictional interference fit which, normally, will require a certain amount of force for disengagement. Needle assembly hubs are commonly made of injection molded plastic while syringes are commonly made of injection molded plastic or glass. The interior of the hub passageway and the exterior of the syringe tip are normally smooth, as manufactured. The smoothness of these surfaces can present problems in achieving a strong frictional interference fit between the syringe tip and the hub. This problem can be compounded if there is liquid on the surface of the tip or the interior of the hub. The presence of liquid may significantly reduce the strength of the fit between the hub and the syringe tip because it may act as a lubricant film. To overcome this deficiency, it is desirable to provide a rougher surface on the syringe tip so that the frictional interference fit will be stronger and the effects of liquid contamination will be minimized. The roughness of a syringe tip can be increased when forming the tip or by roughening the tip surface after formation. For example, it is common practice to subject the tip of a glass syringe barrel to an abrasive blasting step wherein particles, such as aluminum oxide beads, are propelled toward the tip surface, in a fluid stream, to roughen the tip surface. Abrasive blasting procedures and the like have a serious disadvantage in that the debris from the abrasive blasting step must be thoroughly removed in a subsequent operation. Because, syringes are frequently used to inject medication into the human body great care must be taken to insure that foreign particles are removed before the syringe is used in conjunction with a patient. Also, another method of roughening the syringe tip involves the use of a grinding wheel to roughen the exterior surface of the tip. This method also requires a subsequent clean up operation to remove particles generated by the grinding operation.

The instant invention is a significant improvement over the prior art because it provides a coating on the syringe tip for increasing the roughness of the tip. By using a coating, no subsequent clean up step is required and the danger of the clean up step not actually removing all of the loose debris from the syringe, produced during the roughening operation, is eliminated.

Figure 4:
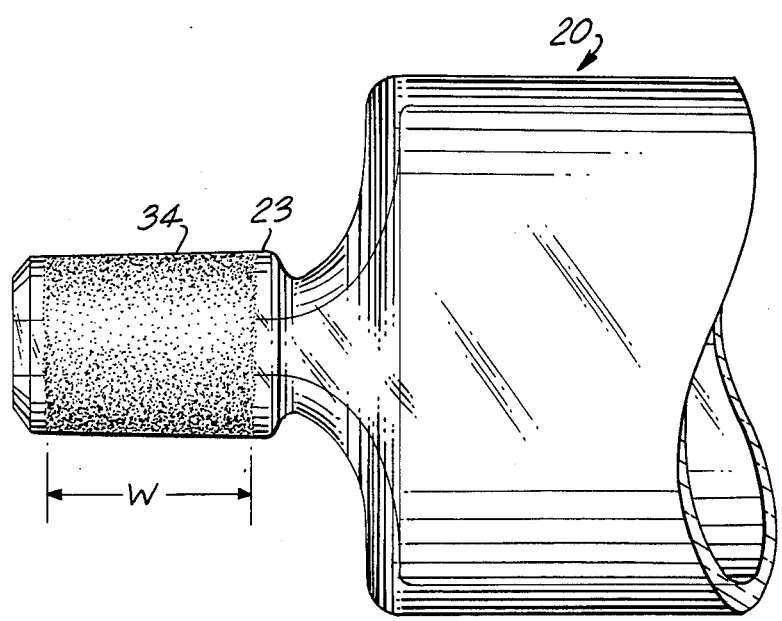
Figure 5:
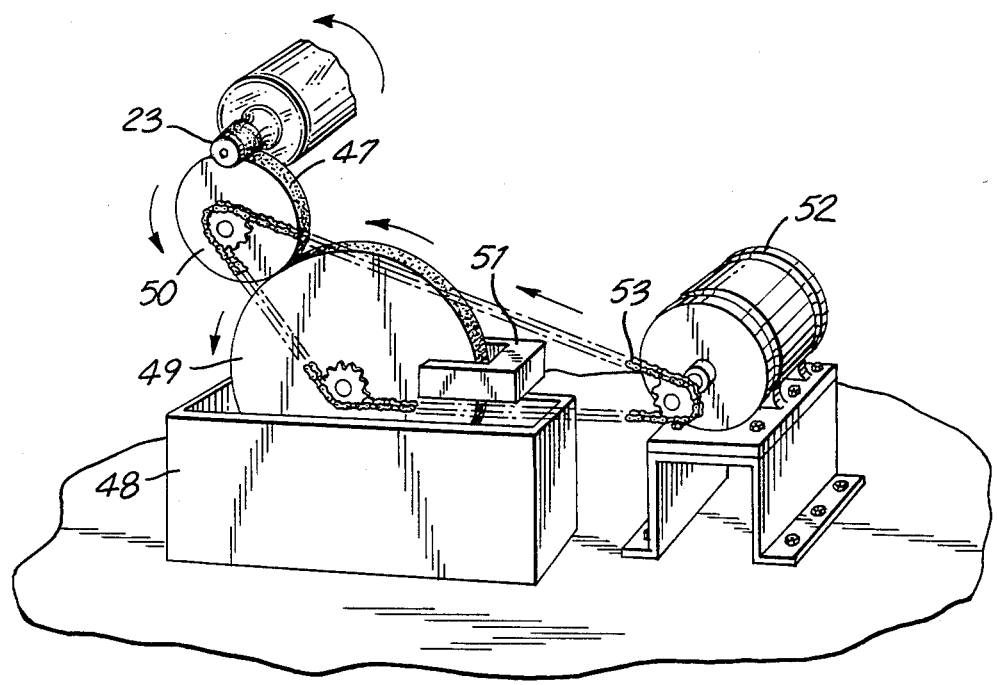

Referring now to FIGS. 4 and 5, the syringe barrel of the preferred embodiment is preferably made of glass and the coating may be applied to the tip by a printing method using the apparatus of FIG. 5. Particularly a suspension 47 including particles suspended in a liquid carrier is contained in reservoir 48. A rotating transfer wheel 49 contacts the suspension in the reservoir, and as it rotates carries the suspension out of the reservoir toward rotating coating or printing wheel 50. The transfer wheel and the printing wheel are driven by motor 52 through a driving means such as chain 53. Control member 51 wipes suspension from the sides of transfer wheel 49 and provides a limited clearance between the outside diameter of the transfer wheel and the control member so that only a thin film of suspension moves along the outside diameter of the transfer wheel. There is a gap between printing wheel 50 and transfer wheel 49. This gap is smaller than the film thickness so that a portion of the film on transfer wheel 49 transfers to printing wheel 50 at the point of tangency. As transfer wheel 50 continues to rotate it carries suspension 47 to the rotating syringe tip where a portion of the film is transferred onto the circumference of the syringe tip. It should be noted that the syringe barrel is rotated by a separate rotating means which can be part of the system which carries the syringe barrel through the forming process. It is preferred that printing wheel 50 be narrower than the length of the frusto-conically shaped tip so that the coating can be applied between the proximal and the distal end of the tip approximately at width W, as best illustrated in FIG. 4.

After the suspension is applied to the syringe tip, the syringe is removed from the printing station and cured, usually by the application of heat, to drive off a portion of the liquid carrier and assure that the solid particles are firmly attached to the tip surface. In the preferred embodiment the particles in the suspension comprise a ceramic powder commonly used to decorate glass articles. Ceramic powders are widely commercially available and include Blythe product No. 49T532 or 49T511 commercially available from Johnson Matthey Inc., Malvern, Pa., U.S.A. The ceramic powder is combined with a carrier such as a commercially available medium oil containing turpentine oils and synthetic resins. One such medium, having a catalog name of MX 54 HPC mixing oil, is available from HPC Degussa Corporation, South Plainfield, N.J., U.S.A. Although the suspension used to make the preferred embodiment comprises particles including ceramic powder, it is within the purview of the present invention to include particles of glass, ceramic, metal or combinations thereof. The suspension should be adjusted to the proper viscosity for the coating method chosen.

With respect to glass syringe barrels, the suspension may be applied to the tip of the barrel during the process that forms the barrel. The syringe can then be transferred to an annealing furnace, which is a common apparatus used in the manufacture of glass articles such as a glass syringe barrel, for a period of time which will cure the suspension by evaporating a portion of the medium oil and causing the ceramic particles to become bonded to the tip of the glass syringe. It will be readily apparent to one skilled in the art that the method described herein can be conveniently inserted into an existing process for the manufacture of a glass syringe barrel and that the same annealing step used in the manufacturing process may be used for the curing step. In fabricating the instant embodiment, the barrel, with coating applied, is passed through an annealing furnace where the temperature ranges from between about 700° C. and 400° C., for a time period of about 2 minutes. It should be noted that a wide variety of time/temperature combinations may be used in the curing step, depending on the size of the syringe and the composition of the coating.

Further, the equipment previously used to remove debris from the roughening process, which has now been eliminated, may be discarded. This step will no longer be necessary because the particles from the coating provide the additional roughness to the tip portion so that the force required to remove a fluid transfer apparatus, such as a hypodermic needle hub, which is removably connected to the tip by a frictional interference fit, is greater than the force required to remove the fluid transfer apparatus from an identically sized tip without the coating of the instant invention.

It will be apparent to one skilled in the art that numerous coatings may be used to improve the roughness of a syringe barrel tip. These coatings may include particles, as described hereinabove, which adhere to the tip to increase the roughness of the tip. Also, the coating may be uniform in nature and applied with a printing wheel which has a pattern on its outside diameter so that the coating is distributed over to the syringe tip in conformity with the pattern. The pattern may include circumferential rings which, when the coating is cured, will increase the roughness of the syringe tip in a direction perpendicular to the rings. It is within the purview of the present invention to include any coating which, when cured or dried, increases the roughness of the tip of the syringe barrel so that the force required to remove a fluid transfer apparatus connected to the tip by a frictional interference fit is greater than the force required to remove the fluid transfer apparatus from the identically sized tip without the coating.

It will also be apparent to one skilled in the art that there are a wide variety of processes which can be used to apply the coating, such as spraying, electrostatic deposition, brushing and the like, and that the process described hereinabove is exemplary of these many possibilities. Further, it is clear that some processes may be ideal for application to a glass barrel but may include process temperatures which would destroy another type of barrel, for example a plastic barrel, accordingly the process and the coating must be chosen carefully to be compatible with the syringe barrel material.

The syringe barrel may be constructed of a wide variety of rigid materials such as metals, plastics, glass and ceramics. It is also within the purview of the present invention to include syringe tips which are constructed of different materials than the barrel portion wherein the tip can be made of a wide variety of rigid materials such as metals, plastics, glass and ceramic materials.

Thus, it can be seen that the present invention provides a simple, straightforward, reliable, easily fabricated syringe barrel wherein the barrel tip includes a coating to increase the roughness of the tip. The present invention eliminates the need for contamination generating abrasive blasting processes, grinding processes or the like and further eliminates the clean up operations necessitated by these debris generating procedures.

What is claimed is:

1. A syringe barrel comprising:
    an elongate barrel portion having a chamber for retaining fluid;
    a tip extending from a distal end of said barrel portion having a passageway therethrough communicating with said chamber; and
    an applied coating on said tip for increasing the roughness of said tip so that the force required to remove a fluid transfer apparatus removably connected to said tip by a frictional interference fit is greater than the force required to remove the fluid transfer apparatus from an identically sized tip without said coating.

2. The syringe barrel of claim 1 wherein said tip is frusto-conically shaped, said tip having a smaller outside diameter at the distal end of said tip than at the proximal end of said tip.

3. The syringe barrel of claim 1 wherein said tip is cylindrically shaped having a substantially uniform outside diameter.

4. The syringe barrel of claim 1 wherein said chamber has a substantially circularly shaped cross section.

5. The syringe barrel of claim 1 wherein said tip is made from material selected from the group consisting of glass, plastic, metal and ceramic materials.

6. The syringe barrel of claim 5 wherein said coating includes particles fixedly attached to the surface of said tip.

7. The syringe barrel of claim 6 wherein said particles are selected from a group consisting of glass, ceramic, metal or combinations thereof.

8. A syringe barrel comprising:
    a barrel portion having a chamber for retaining fluid;
    a tip extending from a distal end of said barrel portion having a passageway therethrough communicating with said chamber; and
    applied coating means adhered to said tip for increasing the roughness of said tip.

9. A syringe barrel comprising:
    an elongate barrel portion having a chamber for retaining fluid;
    a tip extending from a distal end of said barrel portion having a passageway therethrough communicating with said chamber; said tip being frusto-conically shaped, said tip having a smaller outside diameter at the distal end of said tip than at the proximal end of said tip; and
    an applied coating on said tip for increasing the roughness of said tip so that the force required to remove a fluid transfer apparatus removably connected to said tip by a frictional interference fit is greater than the force required to remove the fluid transfer apparatus from an identically sized tip without said coating.

10. The syringe barrel of claim 9 wherein said tip is made from material selected from the group consisting of glass, plastic, metal and ceramic materials.

11. The syringe barrel of claim 10 wherein said coating includes particles fixedly attached to the surface of said tip.

12. The syringe barrel of claim 11 wherein said particles are selected from a group consisting of glass, ceramic, metal or combinations thereof.

13. A method of increasing the roughness of the tip of a syringe barrel so that the force required to remove a fluid transfer apparatus removably connected to the tip by a frictional interference fit is greater than the force required to remove the fluid transfer apparatus from an identically sized tip without the coating comprising:
    (a) selecting, in a selecting step, a syringe barrel including an elongate barrel portion having a chamber for retaining fluid and a tip extending from a distal end of said barrel portion having a passageway therethrough communicating with said chamber;
    (b) depositing, in a coating step, a suspension including a liquid carrier and solid particles so that said suspension is deposited on said tip;
    (c) transferring said syringe barrel to a heated area having a temperature high enough to vaporize a portion of said carrier and to cause said particles to fixedly attach to said tip; and
    (d) removing said syringe barrel from said heated area.

14. The method of claim 13 wherein said coating step includes rotating said tip in close proximity to a rotating printing wheel having an outside diameter coated with said suspension so that said suspension is deposited on said tip.

15. The method of claim 13 wherein said particles are selected from a group consisting of glass, ceramic, metal or combinations thereof.

16. The method of claim 13 wherein said tip is made of material selected from the group consisting of glass, plastic, metal and ceramic materials.

* * * * *